United States Patent [19]

Duggan

[11] 4,402,322

[45] Sep. 6, 1983

[54] PACER OUTPUT CIRCUIT

[75] Inventor: Stephen R. Duggan, Rosemount, Minn.

[73] Assignee: Medtronic, Inc., Minneapolis, Minn.

[21] Appl. No.: 247,481

[22] Filed: Mar. 25, 1981

[51] Int. Cl.³ ............................................. A61N 1/36
[52] U.S. Cl. ............................................. 128/419 PG
[58] Field of Search ................................. 128/419 PG

[56] References Cited

U.S. PATENT DOCUMENTS 3,563,247 2/1971 Bowers .................. 128/419 PG
3,924,641 12/1975 Weiss ...................... 128/419 PG

*Primary Examiner*—William E. Kamm
*Attorney, Agent, or Firm*—Robert C. Beck; John L. Rooney; Joseph F. Breimayer

[57] ABSTRACT

Pacer output circuitry for providing biphasic stimulation pulses to heart tissue at a voltage twice the supply voltage. Additionally, the circuit may be configured to sense the intracardiac electrogram in a unipolar or bipolar configuration.

4 Claims, 3 Drawing Figures

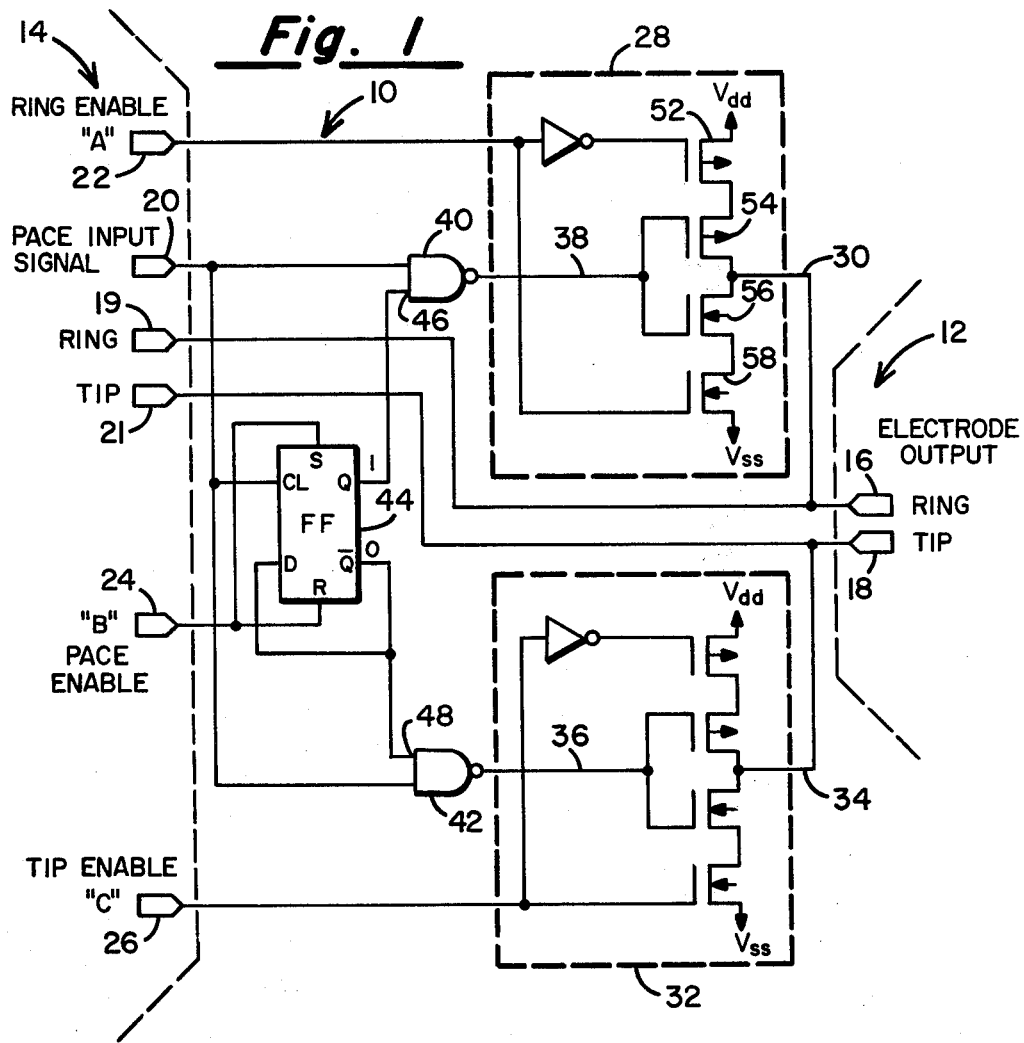
*Fig. 1*
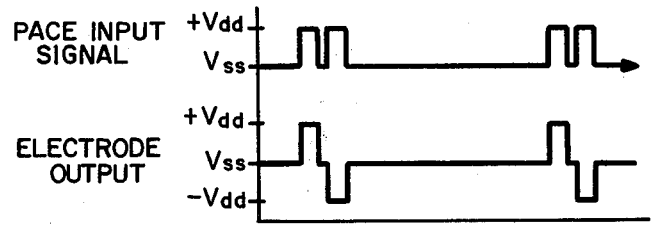
*Fig. 3*
| | "A" | "B" | "C" | | |
|---|---|---|---|---|---|
| PACING MODE | 1 | 0 | 1 | PACE (DIFFERENTIALLY) | |
| SENSING MODES | 0 | 1 | 1 | SENSE (BETWEEN RING AND GND) | UNIPOLAR MODE |
| | 1 | 1 | 0 | SENSE (BETWEEN TIP AND GND) | |
| | 0 | 1 | 0 | SENSE (DIFFERENTIALLY) | BIPOLAR MODE |
*Fig. 2*

PACER OUTPUT CIRCUIT

BACKGROUND OF THE INVENTION

1. Field of the Invention

This invention relates to implantable medical devices and, more particularly, to a pacemaker output circuit for developing stimulating pulses to be coupled to the heart in response to logic level control signals.

2. Description of the Prior Art

Implantable medical devices for the therapeutic stimulation of the heart are well known in the art from U.S. Pat. No. 3,478,746, issued to Wilson Greatbatch, which discloses a demand pacemaker. This form of pacer stimulates cardiac activity in the absence of naturally occurring spontaneous cardiac activity. This operational mode requires a sense amplifier for detecting the naturally occurring deplorizations. Since the stimulating pulses and detected depolarizations are supplied through the same lead system to the cardiac tissue, the output stage of the pacer is electrically in parallel with the sense amplifier input resulting in an undesirable reduction in the input sense amplifier impedance.

Modern versions of the demand pacemaker are powered by lithium primary batteries having voltages in the range of 2 to 3 volts, which is substantially below the nominal voltage of earlier mercury-zinc powered pacemakers. As a consequence, it has been common to incorporate a voltage doubler into the output circuitry to provide higher amplitude stimulation of the cardiac tissue. In prior art pacemakers, this is done by a voltage doubler which charges a capacitor to the battery voltage and then switches this charged capacitor into series with the battery, while the combination of battery and capacitor is coupled to the heart.

This prior art configuration requires a relatively large capacitor (10 microfarad) placed in the output circuitry. This capacitor occupies a substantial volume on the hybrid substrate and poses reliability problems for long-term pacer implants.

SUMMARY OF THE INVENTION

In contrast to this prior art, the pacer output stage of the present invention produces voltage doubling without the necessity for an output capacitor. The circuitry taught may also assume a high impedance configuration which may be used to effectively isolate the output stage of the pacemaker from the sense amplifier during cardiac sensing.

Additionally, the output stage may be configured by enable control signals to permit various combinations of unipolar and bipolar sensing.

The structure of the invention may be implemented in CMOS process technology and may consist of tri-state high current buffers for delivering current to the heart and control logic for controlling the operation of the current buffers.

BRIEF DESCRIPTION OF THE DRAWINGS

FIG. 1 is a schematic representation of the circuitry of the present invention;

FIG. 2 is a truth table showing the operational modes of the present invention; and FIG. 3 is a characteristic waveform illustrating the operation of the invention.

DETAILED DESCRIPTION OF THE PREFERRED EMBODIMENT

Referring to FIG. 1, pacer logic is coupled to the output circuit 10 through a pacer interface 14. A lead which is coupled to the patient's heart is coupled to the output circuit through lead interface 12. The ring 16 and tip 18 electrode connections at the lead interface 12 are duplicated on the pacer interface 14 for connection to a sense amplifier (not shown). The ring enable, pace enable, and tip enable control inputs A, B, and C, respectively, are used to configure the output/input circuit into a sensing or pacing configuration. While in the pacing mode, pace input signals are supplied to connection 20 to initiate the biphasic output pulse produced at the ring and tip electrodes.

The operation of the invention is most easily understood by considering the pacing and sensing operations separately. In the pacing configuration, a differential or biphasic output pulse is provided at the ring and tip electrodes. This output waveform shown as the electrode output of FIG. 3 is developed in response to the pace input signal applied to terminal 20 which is also shown in FIG. 3.

In operation, tri-state current buffers 28 and 32 are used to provide current to the ring and tip electrodes. A tri-state buffer such as that shown as 28 consists of four complementary transistors 52, 54, 56, and 58. The innermost pair of complementary transistors 54 and 56 form an inverter which assumes an output state depending upon the logic level applied to their gates through connection 38. The outermost complementary transistor pair, 52 and 58, cooperate to either connect the inverter pair to the power supply of the pacemaker or to isolate the inverter pair from the power supply voltages Vdd and Vss. In operation a logic 1 at ring enable terminal 22 turns transistor 58 on, and the inverted signal turns transistor 52 on. In this configuration, the transistors 54 and 56 of the inverter are connected to the positive power supply Vdd and the negative power supply Vss. To supply pacing energy to the ring and tip electrodes, both tri-state buffers 28 and 32 are turned on by logic 1 signals provided to ring enable terminal 22 and tip enable terminal 26.

Additionally, in the pacing mode a logic 0 is placed at pace enable terminal 24. This logic level signal permits the flip-flop 44 to be clocked by the pace input signal supplied to pace input terminal 20. In operation, a sequence of input signals to the pace input terminal 20 will produce a sequence of complementary logic signals on inverter gate 38 and inverter gate 36. For example, if the first positive transition of the pace input signal clocked the Q-output of the flip-flop 44 to a logic 1, then a logic 0 would be produced at the inverter gate 38 and a logic 1 would be placed on inverter gate 36. In this configuration, output terminal 30 would be at a logic 1 or +Vdd voltage and output 34 would be at the ground or Vss voltage, thus producing the positive-going transition of the output electrode waveform shown in FIG. 3. During the next positive-going transition of the pace input signal, inverter gate 38 would go to a logic 1 and inverter gate 36 would go to a logic 0 producing the negative-going transition of the electrode output shown on FIG. 3.

In the sensing mode, at least one of the tri-state current buffers 28 or 32 will be "off" in contrast to the pacing configurations where both current buffers are "on." In the sensing mode, the sense amplifier can be connected between either the ring or tip and ground, or the sense amplifier may be connected differentially between the ring and the tip. These unipolar and bipolar sensing modes are controlled by the state of the ring enable A, pace enable B, and tip enable C control inputs. In practice, these alternate sensing modes may be alterable through programming of the pacer or the pacer may be fixed during the manufacturing process into one of these available sensing configurations.

The truth table of FIG. 2 shows the alternate sensing configurations as a function of the input state of the control inputs A, B, and C. For example, to sense between the ring and ground, a logic 0 was placed on control input A and a logic 1 is placed on both control inputs B and C. The logic 1 on control input B forces both the Q and NOTQ output of flip-flop 4 to the logic 1 state, thus producing a logic 1 on inverter inputs 38 and 36. In this configuration, the output of either tri-state buffer 28 or 32 will be connected to the negative supply voltage Vss if that tri-state buffer is on. Thus the logic 1 on tip enable C effectively grounds the tip electrode 18 permitting unipolar sensing between the ring and ground. In an analagous fashion, a logic 1 on the ring enable input 22 will effectively ground the ring connection 16 and permit unipolar sensing between the tip and this ground reference.

If neither of the tri-state current buffers 28 or 32 in on, then the outputs 30 and 34 are effectively isolated from the power supply voltages and the ring and tip electrodes are free to float. In this high-impedance configuration, the sense amplifier will sense differentially between the ring and tip electrodes.

Having thus described the invention, it should be apparent that numerous modifications may be made to the circuitry without departure from the scope of the invention.

What is claimed is:

1. An improved pacer output/input circuit of the type having first
   and second output electrode connections for coupling to the heart, for producing a biphasic stimulation output pulse from single ended power supply and having an output voltage twice that of said power supply in response to pace input signals including:
   a first current limiting buffer for selectively sourcing or sinking current from a first output electrode connection in response to a first control signal;
   a second current limiting buffer for selectively sourcing or sinking current from said second output electrode in response to a second control signal; and
   wherein the improvement comprises: means for producing a time sequence of the complementary first and second control signals in response to a sequence of pace input pulses.

2. The pacer output/input circuit of claim 1 wherein said first and
   second current buffers comprise tristate CMOS inverters having first and second tristate enable inputs for selectively isolating said first and second output electrode connections from said single ended power supply in response to respective first and second enable signals.

3. A pacer output/input circuit of claim 1 or claim 2 wherein said
   means for producing a sequence of complementary control signals includes a bistable flip-flop having first and second complementary outputs coupled to first and second logic gates for producing a time sequence of said first and second control signals in response to a time sequence of pace input pulses supplied to both said gates and said bistable means.

4. A pacer output/input circuit of claim 2 wherein said current
   limiting buffers may be selectively isolated for permitting unipolar or bipolar sensing and biphasic pacing of the heart, through the application of logic level control signals applied to said first and second enable inputs.

* * * * *